United States Patent
Kelly (10) Patent No.: US 11,617,847 B2
(45) Date of Patent: Apr. 4, 2023

(54) METHODS FOR MINIMIZING DELAYED EFFECTS OF EXPOSURE TO REDUCED OXYGEN PARTIAL PRESSURE VIA ADMINISTRATION OF SUPPLEMENTAL OXYGEN

(71) Applicant: Model Software Corporation, New Orleans, LA (US)

(72) Inventor: John J. Kelly, New Orleans, LA (US)

(73) Assignee: MODEL SOFTWARE CORPORATION, New Orleans, LA (US)

( * ) Notice: Subject to any disclaimer, the term of this patent is extended or adjusted under 35 U.S.C. 154(b) by 428 days.

(21) Appl. No.: 16/742,272

(22) Filed: Jan. 14, 2020

(65) Prior Publication Data

US 2020/0169161 A1 May 28, 2020

Related U.S. Application Data

(63) Continuation-in-part of application No. 16/420,709, filed on May 23, 2019, now Pat. No. 10,532,175, (Continued)

(51) Int. Cl.
*A61M 16/10* (2006.01)
*A61M 16/20* (2006.01)
(Continued)

(52) U.S. Cl.
CPC .... *A61M 16/1005* (2014.02); *A61M 16/0078* (2013.01); *A61M 16/024* (2017.08);
(Continued)

(58) Field of Classification Search
CPC .......... A61M 16/0057; A61M 16/0066; A61M 16/024; A61M 16/1005; A61M 16/101;
(Continued)

(56) References Cited

U.S. PATENT DOCUMENTS

| 3,672,384 A | 6/1972 | Hellquist |
| 4,198,213 A | 4/1980 | Mannatt |

(Continued)

FOREIGN PATENT DOCUMENTS

| CN | 109718453 A | 5/2019 | |
| EP | 0808769 A2 * | 11/1997 | ............. B64D 13/00 |

(Continued)

OTHER PUBLICATIONS

EPO Communication Pursuant to Article 94(3) EPC, issued by the European Patent office in EP 17891989.0, dated Aug. 30, 2021.
(Continued)

*Primary Examiner* — Joseph D. Boecker
(74) *Attorney, Agent, or Firm* — Panitch Schwarze Belisario & Nadel LLP (57) ABSTRACT

Described herein are methods which involve minimizing or eliminating the occurrence of delayed negative effects that may arise from exposure to reduced oxygen partial pressure. An amount of supplemental oxygen, which substantially mimics a target oxygen partial pressure, is administered to an individual that is exposed to a reduced oxygen partial pressure environment, to compensate for the reduced oxygen partial pressure. The target partial pressure may be selected such that the individual experiences substantially no change in the oxygen partial pressure. Individuals receiving the supplemental oxygen may be healthy, have special sensitivities, or have a pre-existing neurological condition.

8 Claims, 4 Drawing Sheets

Related U.S. Application Data which is a continuation of application No. 15/864,625, filed on Jan. 8, 2018, now abandoned, which is a continuation of application No. 15/403,240, filed on Jan. 11, 2017, now abandoned.

(51) Int. Cl.
  *A61M 16/00* (2006.01)
  *A61M 16/12* (2006.01)
  *A62B 7/14* (2006.01)
  *A61M 16/06* (2006.01)
  *B64D 13/06* (2006.01)

(52) U.S. Cl.
  CPC ........ *A61M 16/125* (2014.02); *A61M 16/202* (2014.02); *A61M 16/0066* (2013.01); *A61M 16/06* (2013.01); *A61M 16/101* (2014.02); *A61M 2016/1025* (2013.01); *A61M 2202/0208* (2013.01); *A61M 2205/3334* (2013.01); *A61M 2205/3358* (2013.01); *A62B 7/14* (2013.01); *B64D 2013/0681* (2013.01)

(58) Field of Classification Search
  CPC .... A61M 2016/1025; A61M 2230/205; A62B 7/14; B64D 2013/0681
  See application file for complete search history.

(56) References Cited

U.S. PATENT DOCUMENTS

| | | | |
|---|---|---|---|
| 4,210,137 | A | 7/1980 | Henkin |
| 4,651,728 | A | 3/1987 | Gupta et al. |
| 5,247,926 | A | 9/1993 | Harral |
| 5,357,949 | A | 10/1994 | Bertheau et al. |
| 5,590,852 | A | 1/1997 | Olson |
| 5,791,982 | A | 8/1998 | Curry et al. |
| 5,809,999 | A | 9/1998 | Lang |
| 6,024,087 | A | 2/2000 | Kersey et al. |
| 6,244,540 | B1 | 6/2001 | Stabile et al. |
| 6,302,106 | B1 | 10/2001 | Lewis |
| 6,382,563 | B1 | 5/2002 | Chiu |
| 6,669,758 | B1 | 12/2003 | Hart et al. |
| 6,923,183 | B2 | 8/2005 | Martinez et al. |
| 7,040,319 | B1 | 5/2006 | Kelly et al. |
| 7,082,946 | B2 | 8/2006 | Farin et al. |
| 7,246,620 | B2 | 7/2007 | Conroy, Jr. |
| 7,331,343 | B2 | 2/2008 | Schmidt et al. |
| 8,052,087 | B2 | 11/2011 | Jörn |
| 8,474,456 | B2 | 7/2013 | Rittner et al. |
| 8,689,790 | B2 | 4/2014 | Cannon |
| 8,795,041 | B2 | 8/2014 | Saito et al. |
| 9,022,033 | B2 | 5/2015 | Hk |
| 9,345,913 | B2 | 5/2016 | Rittner et al. |
| 2002/0096174 | A1 | 7/2002 | Hill et al. |
| 2002/0139368 | A1 | 10/2002 | Bachinski |
| 2003/0154981 | A1 | 8/2003 | Spruiell |
| 2004/0206353 | A1 | 10/2004 | Conroy, Jr. |
| 2005/0061915 | A1 | 3/2005 | Vogt et al. |
| 2005/0115565 | A1 | 6/2005 | Geary |
| 2005/0126570 | A1 | 6/2005 | Phillips |
| 2006/0068693 | A1 | 3/2006 | Kono et al. |
| 2006/0201504 | A1 | 9/2006 | Singhal et al. |
| 2007/0089746 | A1 | 4/2007 | Mitchell et al. |
| 2009/0044800 | A1 | 2/2009 | Jorn |
| 2009/0165796 | A1 | 7/2009 | Aubonnet et al. |
| 2009/0301489 | A1 | 12/2009 | Bloch et al. |
| 2010/0043788 | A1 | 2/2010 | Fine et al. |
| 2010/0043794 | A1* | 2/2010 | Saito .................. B64D 13/06 128/204.22 |
| 2010/0229864 | A1 | 9/2010 | Vogt et al. |
| 2010/0258127 | A1 | 10/2010 | Hk |
| 2011/0240017 | A1 | 10/2011 | Butler et al. |
| 2011/0290250 | A1 | 12/2011 | Olson et al. |
| 2012/0118285 | A1 | 5/2012 | Wondka et al. |
| 2013/0019865 | A1 | 1/2013 | Gu et al. |
| 2013/0025598 | A1 | 1/2013 | Eiseman |
| 2013/0247913 | A1 | 9/2013 | Aubonnet et al. |
| 2013/0312745 | A1 | 11/2013 | Kshirsagar et al. |
| 2014/0123980 | A1 | 5/2014 | Rissacher et al. |
| 2014/0318989 | A1 | 10/2014 | Dhas |
| 2014/0366875 | A1 | 12/2014 | Motlagh |
| 2015/0157883 | A1 | 6/2015 | Armatorio et al. |
| 2015/0157884 | A1 | 6/2015 | Armatorio et al. |
| 2015/0174359 | A1 | 6/2015 | Elliott et al. |
| 2015/0196245 | A1 | 7/2015 | Peake |
| 2016/0026188 | A1 | 1/2016 | Lanterna et al. |
| 2018/0193584 | A1* | 7/2018 | Kelly ................ A61M 16/1005 |

FOREIGN PATENT DOCUMENTS

| | | |
|---|---|---|
| EP | 0808769 A2 | 11/1997 |
| JP | 2005-518889 A | 6/2005 |
| JP | 2009-062041 A | 3/2009 |
| TW | I548564 B | 9/2016 |
| WO | 03/045782 A1 | 6/2003 |
| WO | 2006106247 A1 | 10/2006 |
| WO | 2015/055672 A1 | 4/2015 |

OTHER PUBLICATIONS

International Search Report (ISR) and Written Opinion issued in PCT/US2021/012923, dated May 12, 2021.

Office Action (Notice of Reasons for Refusal) dated Oct. 5, 2021, by the Japanese Patent Office in corresponding Japanese Patent Application No. 2019-538393 and an English Translation of the Office Action. (5 pages).

Office Action (Decision of Refusal) dated Nov. 12, 2021, by the Taiwan Patent Office in corresponding Taiwanese Patent Application No. 107100843 and an English Translation of the Office Action. (19 pages).

"FAA, "Section I, 1.2—Space"", Available online at<https://www.faa.gov/about/office_org/headquarters_offices/ays/offices/aam/cami/library/online_libraries/aerospace_medicine/tutorial/media/1.1.2_Space.doc>.

"Section I, 1.2—Space", FAA, retrieved from https://www.faa.gov/about/office_org/headquarters_offices/ays/offices/aam/cami/library/online_libraries/aerospace_medicine/tutorial/media/1.1.2_Space.doc.

"State-of-the-art medical equipment", Swiss Air-Ambulance, retrieved from https://web.archive.org/web/20150325132719/https://www.rega.ch/en/swiss-air-ambulance/medical-equipment.aspx with date.

"Swiss Air-Ambulance, "State-of-the-art medical equipment"", Available online at<https://web.archive.org/web/20150325132719/https://www.rega.ch/en/swiss-air-ambulance/medical-equipment.aspx with date> , Mar. 25, 2015.

England, Harvey M, et al., "Comparisons of Molecular Sieve Oxygen Concentrators for Potential Medical Use Aboard Commercial Aircraft", , Jun. 1992, pp. I-7.

England, Jr., Harvey M., et al., "Comparisons of Molecular Sieve Oxygen Concentrators for Potential Medical Use Aboard Commercial Aircraft", DOT/FAA/AM-92/22, Jun. 1992, pp. 1-7.

FAA , "Section I, 1.2—Space", https://www.faa.gov/about/office_org/headquarters_offices/avs/offices/aam/cami/library/online_libraries/aerospace_medicine/tutorial/media/l.1.2_Space.doc.

Franzen, et al., "Le patient comme passager aerien", 698-704.

Franzen, et al., "Le patient comme passager aerien", Forum Med Suisse, vol. 8, No. 38, translation submitted , 2008, pp. 698-704.

Huff, Anndee L, et al., "Sustainable Oxygen: A Low Power Approach for Providing Emergency Medical Oxygen for Spacecraft and Hospitals in Developing Countries", Jul. 1, 2011, pp. I-9.

Huff, Anndee L., et al., "Sustainable Oxygen: A Low Power Approach for Providing Emergency Medical Oxygen for Spacecraft and Hospitals in Developing Countries", Portland State University, PDX Scholar, Mechanical and Materials Engineering, Jul. 1, 2011, pp. 1-9.

PCT/US2017/068069, "Notification of Transmittal of the International Search Report and the Written Opinion Received", 11 pages.

(56) References Cited

OTHER PUBLICATIONS

Seidenberg, et al., "Future Neural", vol. 4, No. 5, Doi:10.2217/fnl.09.32, Sep. 1, 2009.
Seidenberg, et al., "Future Neurol", Doi:10.2217/fnl.09.32. vol. 4(5):, Sep. 1, 2009, pp. 663-668.
Seidenberg, et al., "Future Neurol. Sep. 2009", 663-668.
Swiss Air-Ambulance, "State-of-the-art medical equipment", https://web.archive.org/web/20150325132719/https://www.rega.ch/en/swiss-air-ambulance/medical-equipment.aspx , Mar. 25, 2015.
Translation of Franzen, et al., "Le patient comme passager aerien".
Trevorrow, Tracy, "Air Travel and Seizure Frequency for Individuals With Epilepsy", Seizure, vol. 15, pp. 320-327.
Trevorrow, Tracy, "IR Travel and Seizure Frequency for Individuals With Epilepsy", 2006, pp. 320-327.
Alvarez et al., "Medical Guidelines for Airline Travel, 2nd edition," Aviation, Space, and Environmental Medicine, (May 2003), vol. 74, No. 5, Section II, Supplement, pp. A1-A19, Retrieved from the Internet: URL:https://www.asma.org/asma/media/asma/travel-publications/medguid.pdf. (22 pages).
The extended European Search Report dated Jan. 13, 2020, by the European Patent Office in corresponding European Patent Application No. 17891989.0-1122. (7 pages).
Examination Report dated May 4, 2020, issued by the GCC Patent Office in GC 2018-34593.
Office Action dated Mar. 2, 2021, by the Taiwan Patent Office in corresponding Taiwanese Patent Application No. 107100843. (8 pages).
Search Report dated Oct. 4, 2022 and Written Opinion dated Oct. 5, 2022 in SG10202106581P.
Office Action (Notice of Deficiencies) dated Jun. 29, 2022 in Israeli Application No. 267824.
Notification of Second Office Action, dated Feb. 10, 2023, issued in corresponding Chinese Patent Application No. 201780083052.1, with English language translation, 6 pps.

\* cited by examiner

METHODS FOR MINIMIZING DELAYED EFFECTS OF EXPOSURE TO REDUCED OXYGEN PARTIAL PRESSURE VIA ADMINISTRATION OF SUPPLEMENTAL OXYGEN

CROSS-REFERENCES TO RELATED APPLICATIONS

The present application is a continuation-in-part of U.S. application Ser. No. 16/420,709 filed May 23, 2019, which is a continuation of U.S. application Ser. No. 15/864,625 filed Jan. 8, 2018, which is a continuation of U.S. application Ser. No. 15/403,240 filed Jan. 11, 2017, the contents of each of which are incorporated by reference herein in their entireties.

TECHNICAL FIELD

The present disclosure relates to methods for minimizing the delayed effects of exposure to reduced oxygen partial pressure on an individual, particularly by administering supplemental oxygen for a period of time to compensate for the reduced oxygen partial pressure existing in an environment.

BACKGROUND

Oxygen is critical to human life. Each cell, tissue, and function of the human body requires oxygen. Without oxygen, cells cannot function, repair, and restore. A shortage of oxygen, or hypoxia, can thus cause several problems, some of which carry immediately noticeable effects. Examples of symptoms of hypoxia may include, but are not limited to, nausea, headache, fatigue, and shortness of breath. In severe cases, hypoxia may result in loss of consciousness, seizures, coma, and even death.

High altitudes reduce the partial pressure of oxygen in the lungs. Exposure to a reduced oxygen partial pressure environment, such as in a pressurized aircraft, can thus result in hypoxia. The pressure in an aircraft cabin at altitude is typically maintained at the pressure one would experience at about 7,000 feet (approximately 11 psi). A similar effect is observed in geographic locations at high altitudes. For example, the partial pressure of oxygen is reduced for a high altitude city, such as Denver, Colo., when compared to the partial pressure of oxygen of a city at sea level, such as New Orleans, La. The "station pressure" in Denver is typically about 23-24 inches/hg (about 12 psi) versus the "station pressure" at sea level, which is typically around 30 inches/hg (about 15 psi).

Oxygen accounts for approximately 21% of dry air and the partial pressure of oxygen will decrease in proportion to the decrease in ambient pressure. Accordingly, and by way of example, the partial pressure of oxygen in ambient pressure at sea level is approximately 3.1 psi and will thus proportionally decrease to approximately 2.3 psi in the pressurized aircraft cabin.

A person's sensitivity to reduced oxygen partial pressure environments and/or high altitudes can generally be classified into one of two categories—normal healthy persons and persons having special sensitivities. A normal healthy person will typically not experience side effects from exposure to reduced oxygen partial pressure, such as that observed during air transport on an aircraft at altitude or at a geographic location having a high altitude. A small subset of healthy persons, however, will experience some side effects from exposure to reduced oxygen partial pressure environment, such as that observed during air transport on an aircraft at altitude. This may typically be described as "feeling lousy" after a flight. The other category of individuals includes those with special sensitivities. These persons are individuals who more often than not have pre-existing neurological conditions, such as epilepsy. These persons may or may not experience immediate episodes or symptoms from being at a high altitude, but may instead be susceptible to delayed effects that present following a period of exposure to a reduced oxygen partial pressure environment. One example is that persons with certain forms of epilepsy may not experience symptoms or episodes while exposed to a reduced oxygen partial pressure environment, but instead may have an increased risk of experiencing seizures in a relatively short period of time, up to a few days, following the exposure.

Presently, there are a number of techniques to treat the contemporaneous effects of oxygen deprivation observed from exposure to a reduced oxygen partial pressure environment. One such well-known technique is the administration of supplemental oxygen. When an individual becomes hypoxic after suffering some degree of oxygen deprivation, supplemental oxygen is then supplied to compensate for the observed oxygen deprivation. However, this technique is only applied to address the contemporaneous or immediate effects resulting from the oxygen deprivation. It is not used preventatively to minimize or eliminate the delayed effects of exposure to reduced oxygen partial pressure.

Another similar, well-known technique is administering supplemental oxygen to relieve acute symptoms from exposure to a reduced oxygen partial pressure environment to facilitate/maintain pilot concentration at altitude. In this regard, it is known to provide aircraft pilots with supplemental oxygen to deter the occurrence of a loss of consciousness and/or concentration at high altitudes upon exposure to reduced oxygen partial pressure. Much like the above-mentioned methods for treating hypoxia, supplemental oxygen is provided to abate the immediate effects of oxygen deprivation.

Supplemental oxygen administration also has known applications in treating persons having pre-existing pulmonary conditions. Similar to the treatment of hypoxia, the use of supplemental oxygen for persons having pre-existing pulmonary conditions is therapeutic in nature and contemporaneous to the known condition.

Known oxygen delivery devices are operable to supply oxygen to a person according to one of two ways—at a fixed flow rate or on demand. When oxygen is supplied at a fixed flow rate, the oxygen is typically delivered at a set volume and a set flow rate, regardless of the individual's need for oxygen. This is true when the individual's demand for oxygen is either higher or lower than the amount of oxygen delivered by the set flow rate. In an on demand delivery device, oxygen is supplied to the individual during an inhalation cycle. On demand delivery devices tend to conserve more oxygen than the constant flow rate devices since oxygen is only supplied when the individual inhales rather than continuously free flowing throughout the individual's respiration cycle.

Supplying oxygen also requires controlling the flow rate to meet an individual's demand. This can be effectuated according to any of the several techniques for estimating demand known to those of skill in the art. In some techniques, one or more pressure sensors are placed in relative proximity to an individual's breathing location (e.g., nose or mouth) to measure the ambient pressure and the individual's breathing pressure. The breathing pressure represents the air inhaled and/or exhaled by the individual during a respiration cycle. The measured pressure values are then used to regulate the flow rate. It is common practice for the flow rate to be adjusted such that the pressure differential between the ambient pressure and the breathing pressure is zero. Other exemplary methods for estimating the demand for oxygen involve measuring the amount of carbon dioxide exhausted by the person, measuring the rate of breathing, measuring the flow rate, and measuring the level of activity of a person.

It is also known to control the demand for oxygen by varying the concentration of the oxygen being administered. This is typically effectuated by providing a supply of ambient air mixed with pure oxygen. Since the concentration of oxygen decreases as altitude increases, compensation for this differential can be achieved by increasing the proportion of pure oxygen administered to an individual for a higher altitude.

As indicated above, there are several known techniques for treating the immediate effects of oxygen deprivation. But, these techniques do not consider the negative effects that may occur subsequent to exposure to a reduced oxygen partial pressure environment. Accordingly, there exists a need to develop a preventative measure or technique to compensate for an exposure to a reduced oxygen partial pressure environment in order to minimize or eliminate the occurrence of delayed effects from the exposure, specifically in persons having special sensitivities.

SUMMARY

The present disclosure provides a description of methods for minimizing the delayed effects on an individual resulting from exposure to reduced oxygen partial pressure via the administration of supplemental oxygen. The present disclosure also relates to a post-flight seizure prevention method.

In one embodiment, a method for minimizing delayed effects of exposure to a reduced oxygen partial pressure involves providing a source of supplemental oxygen. Because reduced oxygen partial pressure is known to occur on flights at altitude, the source of supplemental oxygen should be suitable for transport on an aircraft during a flight at altitude. The supplemental oxygen is administered to a person during air transport on the aircraft to compensate for the reduced oxygen partial pressure that exists in the aircraft during the flight. Further, the supplemental oxygen is administered to maintain a target oxygen partial pressure for a period of time such that the person receiving the supplemental oxygen experiences substantially no change in the oxygen partial pressure. The target oxygen partial pressure is an oxygen partial pressure to which the person receiving the supplemental oxygen is routinely accustomed or acclimatized.

In another embodiment, a method for minimizing delayed effects of exposure to a reduced oxygen partial pressure involves providing a portable source of supplemental oxygen. An amount of supplemental oxygen that closely mimics a target oxygen partial pressure is administered to an individual presently exposed to a reduced oxygen partial pressure. The supplemental oxygen is administered to maintain a target oxygen partial pressure for a period of time such that the person receiving the supplemental oxygen experiences little to no change in the oxygen partial pressure. The target oxygen partial pressure is an oxygen partial pressure to which the person receiving the supplemental oxygen is routinely accustomed or acclimatized.

In yet another embodiment, there is disclosed a post-flight seizure prevention method. The post-flight seizure prevention method involves providing a portable source of supplemental oxygen suitable for transport on an aircraft during a flight at altitude and administering the supplemental oxygen to a person during air transport on the aircraft to compensate for a reduced oxygen partial pressure existing in the aircraft during the flight. The supplemental oxygen is administered in an amount such that the person receiving the supplemental oxygen experiences an oxygen partial pressure that substantially mimics a target oxygen partial pressure. In some instances, the target oxygen partial pressure is an oxygen partial pressure to which the person receiving the supplemental oxygen is routinely accustomed or acclimatized.

DETAILED DESCRIPTION

The methods presented herein seek to address the delayed effects that may arise from an individual's exposure to a reduced oxygen partial pressure environment. These methods are preventative in nature and involve steps to compensate in real-time for the reduced oxygen partial pressure environment to either minimize or eliminate the negative physiological effects that can result from exposure to reduced oxygen partial pressure.

Figure 1:
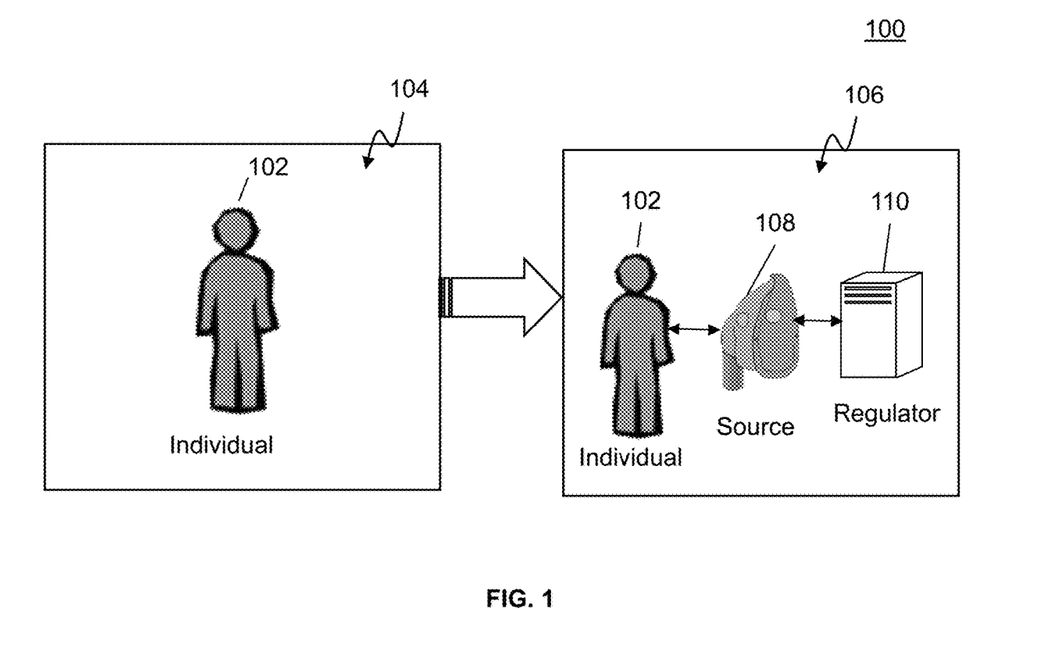
FIG. 1 is a block diagram illustrating a system for providing a source of supplemental oxygen to minimize delayed effects of exposure to a reduced oxygen partial pressure in accordance with exemplary embodiments.

In one embodiment, the delayed effects resulting from exposure to a reduced oxygen partial pressure 106 are mitigated by administering an amount of supplemental oxygen to an individual 102. The source 108 of the supplemental oxygen is not limited to any particular device, but in some embodiments it is preferable that the source be portable. The portability of the supplemental oxygen will afford the individual 102 receiving the supplemental oxygen some level of mobility. In other embodiments, it is preferable that the source 108 of the supplemental oxygen is not separately portable, but is instead mounted to or installed directly within a transportation vehicle. For example, the source 108 of supplemental oxygen may be built-in to the cabin of an aircraft, such that the supplemental oxygen is deliverable to individual seats or sections of the aircraft. It is also contemplated that the transportation vehicles are not limited solely to aircraft vehicles. Such vehicles may include any of those which traverse or encounter a reduced oxygen partial pressure environment.

The amount of supplemental oxygen that is supplied to the individual 102 exposed to the reduced oxygen partial pressure environment 106 is set to provide a target oxygen partial pressure. Ideally, the target oxygen partial pressure is set to mimic the typical oxygen partial pressure environment 104 to which the individual 102 is normally accustomed. The typical oxygen partial pressure environment 104 to which the individual 102 is normally accustomed may also be understood to be the individual's home oxygen partial pressure. For the purposes of this disclosure, the oxygen partial pressure to which the individual 102 is normally accustomed and home oxygen partial pressure may be used interchangeably.

For example, if the individual 102 spends most of his/her time at sea level, the target oxygen partial pressure would be set to be the same as the oxygen partial pressure at sea level (approximately 3 psi). In other words, the home oxygen partial pressure would be 3 psi. The target partial pressure is set in this manner such that the individual 102 receiving the supplemental oxygen ideally experiences a zero net differential oxygen partial pressure between the reduced oxygen partial pressure environment 106 to which he/she is presently exposed and the home oxygen partial pressure environment 102, or at least at a net differential oxygen partial pressure at a low enough level to be effective for mitigating risk of hypoxia by materially reducing the net differential of the oxygen partial pressure that is experienced with respect to what is desired to the extent practical. Regulating, by a regulator 110, the target oxygen partial pressure such that there is a zero net differential oxygen partial pressure with respect to the reduced oxygen partial pressure environment 106 essentially has the effect of negating any impact the reduced oxygen partial pressure environment 106 exerts on the individual 102. Even though the individual 102 is exposed to a reduced oxygen partial pressure environment 106, the individual 102 experiences substantially no change in oxygen partial pressure from his/her home oxygen partial pressure environment 104.

The ideal scenario is one in which an individual 102 experiences a zero net differential oxygen partial pressure. It is not unforeseeable that a zero net differential oxygen partial pressure may not be obtainable. It may not be possible to obtain a zero net differential oxygen partial pressure for some portion of time during the course of the administration of the supplemental oxygen. It may also not be possible to achieve a zero net differential oxygen partial pressure at any point during the duration of the supplemental oxygen administration. However, the methods described herein may be used to minimize the net differential oxygen partial pressure to some extent. It is contemplated that any level of minimization of the net differential oxygen partial pressure between the reduced oxygen partial pressure environment 106 to which an individual 102 is presently exposed and the home oxygen partial pressure 104 using the methods described herein is preferable to no offset.

It is further contemplated that a surplus of supplemental oxygen may be supplied to an individual 102 using any of the methods described herein. A surplus of supplemental oxygen may be understood as a supply of pure oxygen. Supplying pure oxygen to an individual 102 to compensate for exposure to a reduced oxygen partial pressure environment is acceptable within the metes and bounds of the methods discussed here provided that the pure oxygen is administered short term. Short term administration may be understood as a period of time up to and including a number of hours. For example, pure oxygen may be supplied for a period not to exceed 24 hours (or one day). An upper limit of the specific number of hours may vary by individual 102, but pure oxygen should not be administered for a long enough duration to trigger negative effects in the individual receiving the oxygen.

The target oxygen partial pressure may also be an oxygen partial pressure that is not the person's home oxygen partial pressure. Instead, the target oxygen partial pressure may be set to be an oxygen partial pressure to which the person 102 is presently or temporarily acclimatized. For example, an individual's home oxygen partial pressure may be the oxygen partial pressure at sea level (approximately 3 psi), while the individual's acclimatized partial pressure is the oxygen partial pressure at a higher altitude (e.g., 2.8 psi).

It is desirable that the target oxygen partial pressure is adjustable in the disclosed methods. In some embodiments, it is preferable for the target oxygen partial pressure to remain constant while in other embodiments it is preferable for the target oxygen partial pressure to vary over the course of the administration of the supplemental oxygen.

An initial target oxygen partial pressure may be set to the oxygen partial pressure to which the individual 102 receiving the supplemental oxygen is acclimatized. For example, the initial target oxygen partial pressure could be set to the oxygen partial pressure at sea level (approximately 3 psi). If, by way of example, the individual 102 is traveling to a location having a reduced oxygen partial pressure (e.g., higher altitude), it may be desirable to gradually compensate for the shift in oxygen partial pressure between locations. In this case, the higher altitude location could be said to have an end target oxygen partial pressure of approximately 2.6 psi. To compensate for the reduction in oxygen partial pressure from the initial location to the end destination, the target oxygen partial pressure may be gradually varied during the course of administration of supplemental oxygen from 3 psi to 2.6 psi. The change in target oxygen partial pressure can be effectuated either automatically or manually.

In another embodiment, the delayed effects resulting from exposure to a reduced oxygen partial pressure on an aircraft at altitude are mitigated by administering an amount of supplemental oxygen to an individual 102. The source 108 of the supplemental oxygen is not limited to any particular device, but should be approved for transport on an aircraft during a flight at altitude. One exemplary portable source 108 of supplemental oxygen is the Invacare® XPO2 Portable Oxygen Concentrator (Product ID: XPO100). In some embodiments, it is preferable that the source 108 of the supplemental oxygen is not separately portable, but is instead mounted to or installed directly within the aircraft. An amount of supplemental oxygen is administered to the individual 102 during air transport on the aircraft to compensate for the reduced oxygen pressure existing in the aircraft during the flight.

The amount of supplemental oxygen that is supplied to the individual 102 is set (e.g., via the regulator 110) to provide a target oxygen partial pressure. Similar to that discussed above, the target oxygen partial pressure can be constant or adjustable. Ideally, the target oxygen partial pressure is set such that the individual 102 receiving the supplemental oxygen experiences no change in the oxygen partial pressure from the departure location to the arrival location. Depending on the duration of the flight and/or the equipment, a zero net differential in oxygen partial pressure may not be obtainable. Compensation may only be available for a portion of the flight rather than its entirety. Regardless, some amount of compensation for the reduced oxygen partial pressure at altitude is preferable to no compensation.

Under-compensation or temporary overcompensation of the reduced oxygen partial pressure may occur. In either case, administration of supplemental oxygen, whether it undercompensates or overcompensates for the reduced oxygen partial pressure environment is preferable to providing no compensation whatsoever.

In some embodiments, it may be problematic to deliver a too high of a level of oxygen when administering supplemental oxygen. For example, a person 102 that is climbing a mountain or is otherwise exposed to a reduced oxygen partial pressure for a significant period of time (e.g., days, weeks, etc.) may not be able to receive pure oxygen as supplemental oxygen for the duration of their exposure. In such embodiments, the supplemental oxygen may be enriched to a selected concentration, such as one that is not pure (e.g., not 100%) oxygen. For instance, oxygen may be enriched with other air to supplement the individual 102 to achieve the ideal oxygen partial pressure while reducing the opportunity for overexposure to pure oxygen. In an example, a device 108 for delivering supplemental oxygen may include a first tube that delivers pure oxygen with a second tube that delivers ambient air, where the output of the tubes are mixed in a predetermined ratio to achieve the desired oxygen partial pressure. In such an example, the predetermined ratio may be varied via electric or manual modification to the flow rate of pumps for each tube (e.g., via the regulator 110), varying of the input/output orifices of each tube, etc. For instance, the device (e.g., the source 108 and regulator 110) may include an oxygen sensor that measures the output, which may be configured to electronically modify the flow rate of one or both tubes to ensure the output is suitable for achieving the desired oxygen partial pressure level.

Figure 2:
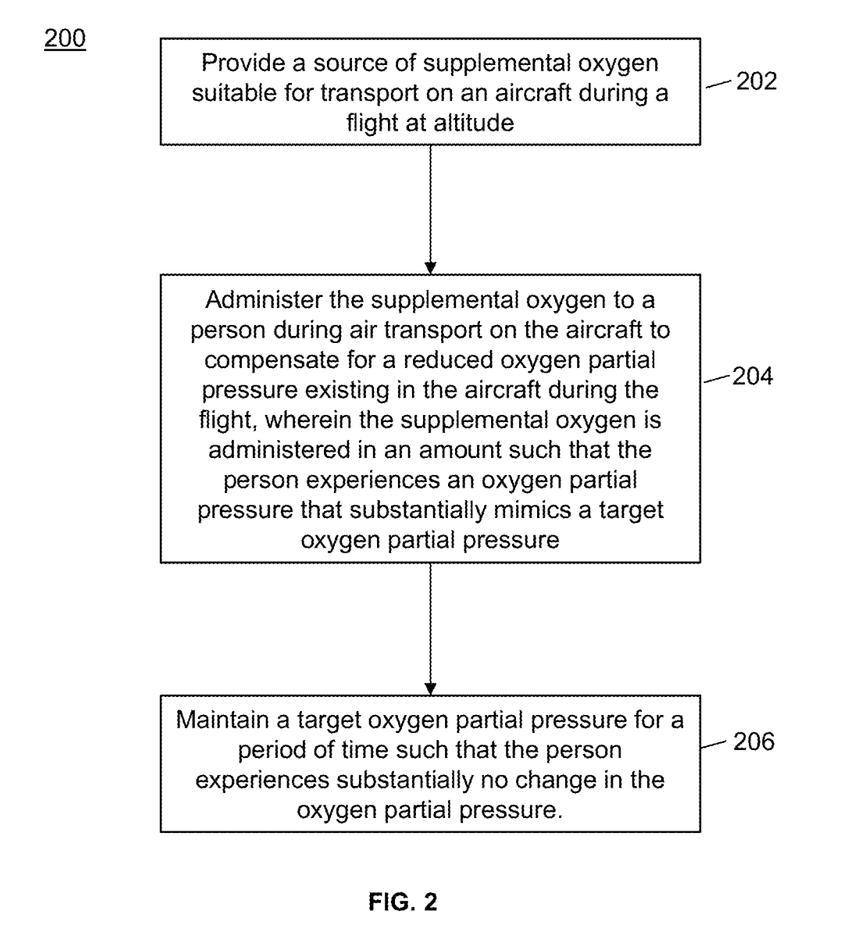
FIG. 2 is a flow chart illustrating an exemplary method for post-flight seizure prevention in accordance with exemplary embodiments.

In yet another embodiment, supplemental oxygen is administered as a preventative measure against the occurrence of one or more post-flight seizures. For instance, FIG. 2 illustrates a method 200 for the prevention of post-flight seizures via the use of supplemental oxygen. In step 202, a source 108 of supplemental oxygen that is suitable for transport on an aircraft during a flight at altitude, but is not particularly limited to any one specific device, is provided. In some embodiments, the source 108 of supplemental oxygen is a portable device. In other embodiments, it is preferable that the source 108 of the supplemental oxygen is not separately portable, but is instead mounted to or installed directly within the aircraft. In step 204, an amount of supplemental oxygen is administered to a person 102 during air transport on the aircraft to compensate for the reduced oxygen pressure existing in the aircraft during the flight. This amount of supplemental oxygen is set to provide a target oxygen partial pressure. Similar to that already discussed, the target oxygen partial pressure can be constant or adjustable. However, the target oxygen partial pressure is ideally set such that the individual receiving the supplemental oxygen experiences no change in the oxygen partial pressure from the departure location (e.g., departure airport or starting point of the travel which may be at a different altitude than the airport) to the arrival location (e.g., arrival airport or ultimate destination of the travel such as a ski resort in the mountains above the arrival airport). In some embodiments, the method 200 may include step 206, where the target oxygen partial pressure may be maintained for a period of time such that the person 102 experiences substantially no change in the oxygen partial pressure.

The post-flight seizure prevention method may also involve the acquisition and return of the portable oxygen source 108. Particularly, the post-flight seizure prevention method may include the additional step of obtaining the portable source 108 of supplemental oxygen from a designated location in or in a market area around a departure location prior to departure, for example, although remote ordering and delivery services are also possibilities. The post-flight seizure prevention method may further include returning the portable source 108 of supplemental oxygen to a designated location in an arrival location following landing.

In any of the embodiments described herein, the target oxygen partial pressure may be set as the oxygen partial pressure of an initial location 104, also referred to as a departure city, of the person 102 receiving the supplemental oxygen. Conversely, the target oxygen partial pressure may be set as the oxygen partial pressure of an end location 106, also referred to as an arrival city. The target oxygen partial pressure may also be set, in any of the described embodiments, to the oxygen partial pressure which corresponds to the location 104 where the person 102 receiving the supplemental oxygen is normally accustomed. This may the person's home city.

In any of the embodiments described herein, the target oxygen partial pressure may be constant or variable during the course of the administration of supplemental oxygen. When the target oxygen partial pressure is variable over the course of the administration, the variance can be effectuated by any manner known in the field.

In any of the disclosed embodiments, the administration of supplemental oxygen, whether it undercompensates or overcompensates for the reduced oxygen partial pressure environment is preferable to providing no compensation whatsoever. In this regard, the supplemental oxygen may be administered for the entire period of time when the individual 102 is exposed to reduced oxygen partial pressure. Alternatively, the supplemental oxygen may be administered for only a subset of the time period during which the person 102 is exposed to reduced oxygen partial pressure. Supplemental oxygen may be administered continuously or intermittently in any scenario.

The methods described herein seek to minimize or eliminate the delayed negative effects on a person's physiology resulting from exposure to reduced oxygen partial pressure for some period of time. Although directed to accommodate otherwise healthy individuals 102 who have special sensitivities to reduced oxygen partial pressure environments 106 and persons 102 having pre-existing neurological conditions, such as epilepsy, no individual 102 is exempt from seeking the benefit of the methods described herein. The administration of supplemental oxygen may, in addition to preventing the delayed effects of exposure to a reduced oxygen partial pressure environment 106 as described herein, be employed by a healthy person 102, for example, to facilitate work productivity, enhance concentration, or the like while at altitude.

An apparatus embodying the method preferably supplies a sufficient quantity of mixed air that has a target partial pressure of oxygen, as opposed to supplying a sufficient quantity of pure oxygen so that when combined with the ambient air, it has the desired target partial pressure. In the latter approach, the user could, by getting too high a flow rate of pure oxygen, get a higher than desirable partial pressure of oxygen and thereby be susceptible to suffer some of the injuries caused by too much oxygen. With the former approach, the apparatus would supply the correct target partial pressure, such that if the flow rate is too low, then the partial pressure of oxygen is effectively reduced (because the user would be breathing more cabin air), but possibly not by a material amount. Moreover, if the total flow rate is too high, then some of the mixture is wasted but the oxygen partial pressure is not too high so the risk of adverse consequences due to too much oxygen are mitigated.

Figure 3:
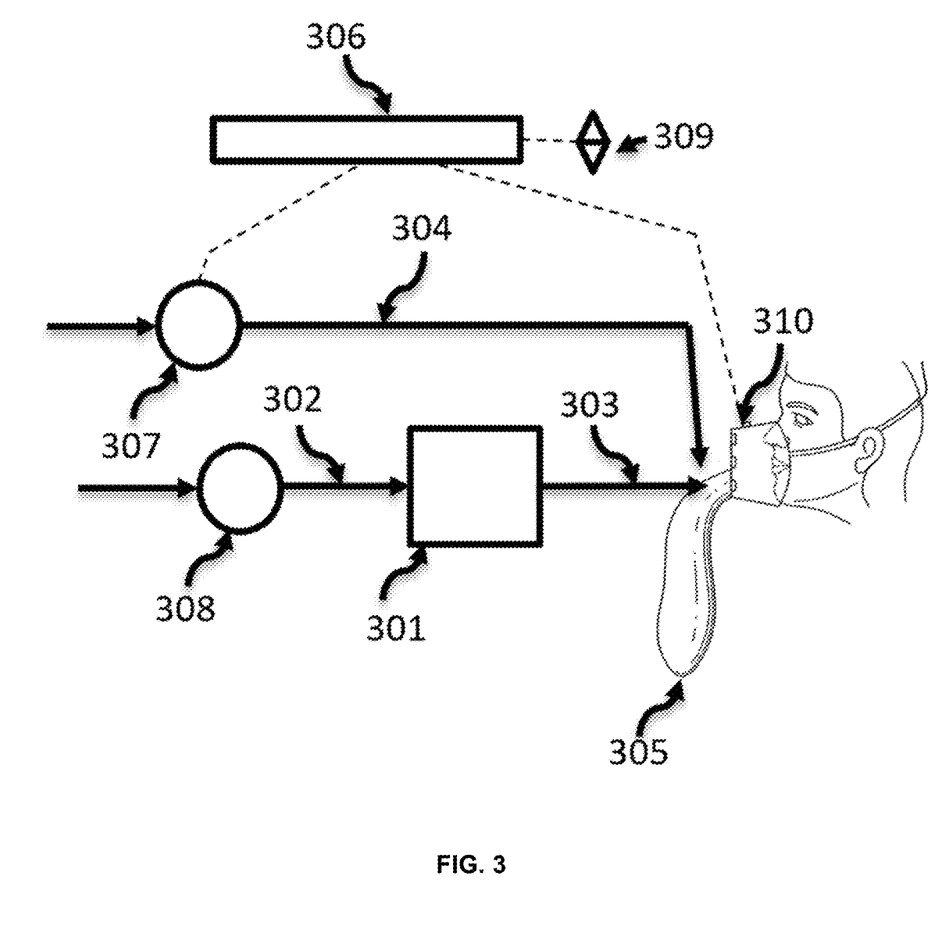
FIG. 3 is a schematic view of a post-flight seizure prevention apparatus according to a first embodiment.

An exemplary apparatus in this regard is illustrated in FIG. 3. The apparatus includes an oxygen concentrator 301 configured to receive non-oxygen enriched air from a conduit 302, to convert the non-oxygen enriched air to oxygen-enriched air, and to discharge a stream of oxygen-enriched air into a conduit 303. Examples of oxygen concentrator 301 can be found in U.S. 2008/0072907, U.S. 2008/0110338, U.S. 2012/0266883, U.S. 2014/0137741, U.S. 2012/0285454, for example, herein incorporated by reference for all purposes.

Furthermore, to accommodate the pulsed flow of the oxygen-enriched air in conduit 303 discharged from the oxygen concentrator 301, the apparatus also includes a conduit 304 configured to supply a stream of non-oxygen enriched air, and a mixer 305 (e.g., plenum bag or chamber or other structure that has a large enough volume or other mechanisms to compensate for brief mismatches in the input and output rates) configured to mix the stream of oxygen-enriched air and the stream of non-oxygen enriched air into a mixture and to discharge the mixture to a person. The mixer 305 can be a known, commercially available concentration mask and so its structural details are not further described herein.

Additionally, the apparatus includes a controller 306 configured to automatically adjust a partial pressure of oxygen in the mixture to a predetermined partial pressure. In this regard, in the embodiment, an ambient pressure sensor 309 is provided and operatively connected to the controller 306 to determine a desired (predetermined) partial pressure, and a sensor 310 configured to sense the partial pressure of the oxygen in the mixture, so that the flow of oxygen can be adjusted through feedback control (as discussed in more detail below) in order to compensate in proportion to the current altitude.

In the embodiment of FIG. 3, a pump 307 is provided which intakes cabin air, pressurizes the cabin air, and discharges the cabin air into the conduit 304 to provide the stream of non-oxygen enriched air to the conduit 304, and a separate pump 308 intakes cabin air, pressurizes the cabin air, and discharges the cabin air into the oxygen concentrator 301 to provide non-oxygen enriched air to the oxygen concentrator 301. The output of the pump 307 is adjustable (such as by adjusting its speed or adjusting an adjustable flow rate valve), and the controller 306 is configured to adjust the output of the pump 307 by feedback control based on the reading of the sensor 310 so that the oxygen partial pressure becomes the desired partial pressure as determined by the reading of the sensor 309. The controller 306 includes, for example, a computer having a program code stored in a storage which is a non-transitory computer readable medium, and is operatively connected to receive signals from the apparatus' various sensors and transmit actuation signals to the portions of the apparatus discussed above. The embodiment of FIG. 4 includes an oxygen concentrator 401, conduit 403 for a stream of oxygen-enriched air, conduit 404 for a stream of non-oxygen enriched air, mixer 405, ambient pressure sensor 409, and oxygen sensor 410 which function in the same manner as those features of the embodiment of FIG. 3, and so their details are not described again with reference to FIG. 4. However, in the apparatus of the FIG. 4 embodiment, there is a single pump 412 which, as explained in detail below pressurizes both the non-oxygen enriched air in conduit 404 and the non-oxygen enriched air supplied to the oxygen concentrator 412.

Figure 4:
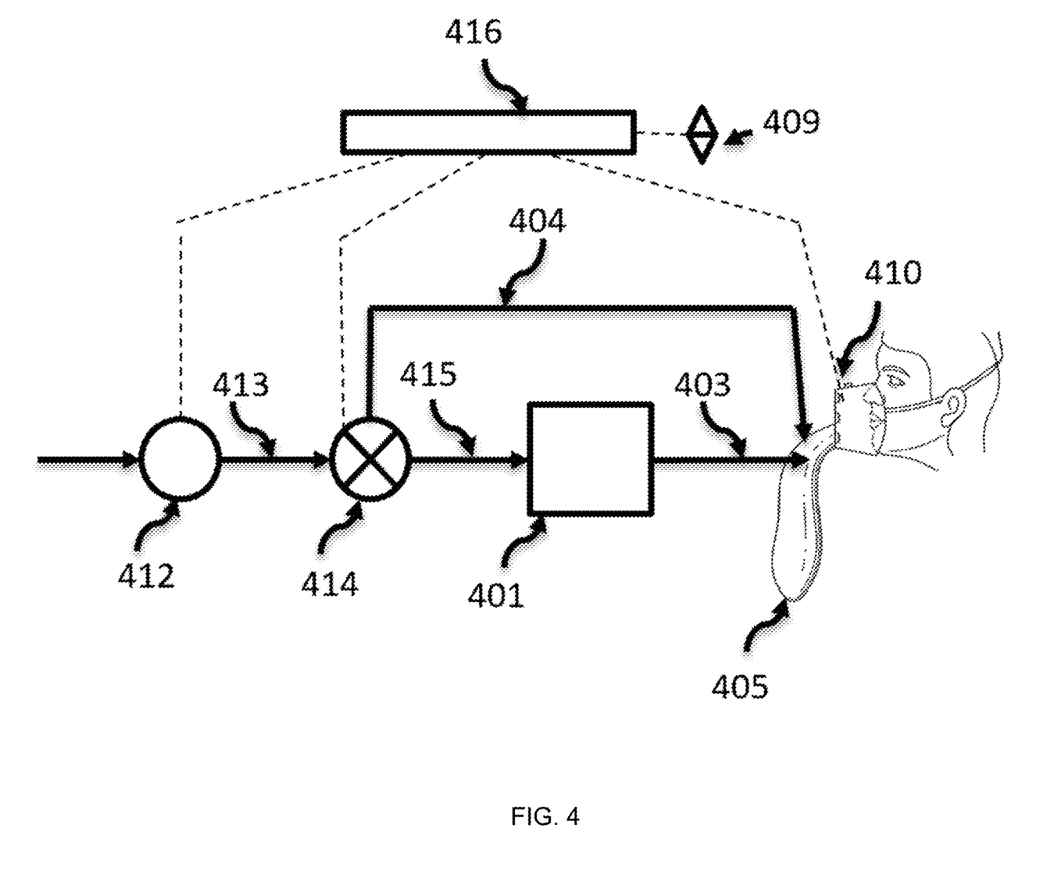
FIG. 4 is a schematic view of a post-flight seizure prevention apparatus according to a second embodiment.

In particular, the non-oxygen enriched air from the pump 412 is provided to a bypass valve 413 via a conduit 414. The bypass valve 413 splits the flow into a main portion in conduit 415 which supplies the non-oxygen enriched air to the oxygen concentrator 412, and a bypass portion to the conduit 404. The bypass valve 413 can be adjusted to control proportions of non-oxygen enriched air fed to the oxygen concentrator 401 and to the conduit 404. Accordingly, in the embodiment in addition to or as an alternative to adjusting the output of the pump 412, the controller 416 of the embodiment can automatically adjust the partial pressure of the oxygen in the mixture by adjusting the bypass valve 413 to adjust the proportion of non-oxygen enriched air fed to the oxygen concentrator 401 and to the conduit 404.

Techniques consistent with the present disclosure provide, among other features, methods for minimizing the delayed effects of exposure to reduced oxygen partial pressure. While various exemplary embodiments of the disclosed system and method have been described above it should be understood that they have been presented for purposes of example only, not limitations. It is not exhaustive and does not limit the disclosure to the precise form disclosed. Modifications and variations are possible in light of the above teachings or may be acquired from practicing of the disclosure, without departing from the breadth or scope.

What is claimed is:

1. A post-flight seizure prevention apparatus comprising:
    an oxygen concentrator configured to receive non-oxygen enriched air, to convert the non-oxygen enriched air to oxygen-enriched air, and to discharge a stream of oxygen-enriched air;
    a conduit configured to supply a stream of non-oxygen enriched air;
    a mixer mask configured to mix the stream of oxygen-enriched air and the stream of non-oxygen enriched air into a mixture and to discharge the mixture to a person; and
    a controller configured to automatically adjust a partial pressure of oxygen in the mixture to a predetermined partial pressure.

2. The post-flight seizure prevention apparatus of claim 1, further comprising a sensor configured to sense the partial pressure of the oxygen in the mixture, wherein
    the controller is configured to automatically adjust the partial pressure of the oxygen in the mixture based on the partial pressure of the oxygen in the mixture sensed by the sensor.

3. The post-flight seizure prevention apparatus of claim 1, further comprising a pump configured to pressurize the stream of non-oxygen enriched air in the conduit.

4. The post-flight seizure prevention apparatus of claim 3, wherein the controller is configured to automatically adjust the partial pressure of the oxygen in the mixture by adjusting an output of the pump.

5. The post-flight seizure prevention apparatus of claim 3, wherein:
    the pump also pressurizes the non-oxygen enriched air received by the oxygen concentrator; and
    the apparatus further comprises a bypass valve downstream of the pump, the bypass valve being configured to control a proportion of non-oxygen enriched air fed to the oxygen concentrator and to the conduit.

6. The post-flight seizure prevention apparatus of claim 5, wherein:
    the controller is configured to automatically adjust the partial pressure of the oxygen in the mixture by adjusting the bypass valve to adjust the proportion of non-oxygen enriched air fed to the oxygen concentrator and to the conduit.

7. The post-flight seizure prevention apparatus of claim 1, wherein the mixer comprises a plenum.

8. The post-flight seizure prevention apparatus of claim 1, further comprising an ambient pressure sensor, wherein the predetermined partial pressure is determined based on the ambient pressure sensed by the ambient pressure sensor.

* * * * *